(12) United States Patent
Chiu et al.

(10) Patent No.: US 8,829,172 B2
(45) Date of Patent: Sep. 9, 2014

(54) MULTIPLEX BARCODED PAIRED-END DITAG (MBPED) SEQUENCING APPROACH AND ITS APPLICATION IN FUSION GENE IDENTIFICATION

(75) Inventors: Kuo Ping Chiu, Taipei (TW); Yi Chou, Taipei (TW); Sheng-Chung Chen, Taipei (TW)

(73) Assignee: Academia Sinica, Taipei (TW)

( * ) Notice: Subject to any disclaimer, the term of this patent is extended or adjusted under 35 U.S.C. 154(b) by 170 days.

(21) Appl. No.: 13/416,764

(22) Filed: Mar. 9, 2012

(65) Prior Publication Data

US 2012/0231508 A1   Sep. 13, 2012

Related U.S. Application Data

(60) Provisional application No. 61/451,613, filed on Mar. 11, 2011.

(51) Int. Cl.
| | |
|---|---|
| C07H 21/00 | (2006.01) |
| G01N 33/487 | (2006.01) |
| C12P 19/34 | (2006.01) |
| C12N 15/66 | (2006.01) |
| C12N 15/65 | (2006.01) |

(52) U.S. Cl.
CPC ............... *C12N 15/66* (2013.01); *C12P 19/34* (2013.01); *C12N 15/65* (2013.01)
USPC .......................................... 536/23.1; 435/6.1

(58) Field of Classification Search
None
See application file for complete search history.

(56) References Cited

U.S. PATENT DOCUMENTS

2008/0124707 A1 *   5/2008   Ruan et al. ................ 435/6
2011/0015096 A1      1/2011   Chiu

OTHER PUBLICATIONS

Fullwood et al. (Current Protocols in Molecular Biology, 2010, 21.15.1-21.15.25).*
Ng et al. (Nature Methods, 2005, 2(2):105-111 and Supplemental Method, Dec. 2004, p. 1-14.*
Shibata et al. (Genome Medicine, 2010, 2:70, p. 1-13).*

* cited by examiner

*Primary Examiner* — Stephanie K Mummert
(74) *Attorney, Agent, or Firm* — Hsiu-Ming Saunders; Intellectual Property Connections, Inc.

(57) ABSTRACT

A method of generating a barcoded Paired-End Ditag (bPED) nucleic acid fragment is disclosed. The method comprises: a) performing a first ligation by ligating a half-adaptor with one or two 3'-overhanging ends to a target nucleic acid to obtain a nucleic acid fragment with two ends each attached to one of the half-adaptor, the half adaptor comprising a half-barcode and a restriction enzyme (RE) recognition site; b) performing a second ligation by ligating two of the half-adaptor at the two ends of the nucleic acid fragment to form a circularized nucleic acid construct, wherein the circularized nucleic acid construct comprises a full-size barcoded adaptor; and c) digesting the circularized nucleic acid construct with a RE that cleaves at a defined distance from the RE recognition site, and thereby generating the bPED nucleic acid fragment.

20 Claims, 5 Drawing Sheets

SEQUENCE LISTING

```
<160> NUMBER OF SEQ ID NOS: 3

<210> SEQ ID NO 1
<211> LENGTH: 10
<212> TYPE: DNA
<213> ORGANISM: Artificial Sequence
<220> FEATURE:
<223> OTHER INFORMATION: Short Oligo w/o T

<400> SEQUENCE: 1
agactccgac                                                            10

<210> SEQ ID NO 2
<211> LENGTH: 11
<212> TYPE: DNA
<213> ORGANISM: Artificial Sequence
<220> FEATURE:
<223> OTHER INFORMATION: Short Oligo with T

<400> SEQUENCE: 2
agactccgac t                                                          11

<210> SEQ ID NO 3
```

```
<211> LENGTH: 14
<212> TYPE: DNA
<213> ORGANISM: Artificial Sequence
<220> FEATURE:
<223> OTHER INFORMATION: Long Oligo

<400> SEQUENCE: 3
gtcggagtct gcgc                                                        14
```

MULTIPLEX BARCODED PAIRED-END DITAG (MBPED) SEQUENCING APPROACH AND ITS APPLICATION IN FUSION GENE IDENTIFICATION

REFERENCES TO RELATED APPLICATION

The present application claims priority to U.S. Provisional Application Ser. No. 61/451,613, filed Mar. 11, 2011, which is herein incorporated by reference in its entirety.

FIELD OF THE INVENTION

The present invention relates generally to the field of ultra high throughput sequencing technology.

BACKGROUND OF THE INVENTION

Paired-End diTag (PET) directly links the 5' terminal tags (~18-20 bp each) of genomic DNA fragments or cDNA molecules to their corresponding 3' terminal tags for high throughput sequencing. It has led to a number of important discoveries including fusion gene identification (Ng P et al. "Gene identification signature (GIS) analysis for transcriptome characterization and genome annotation" *Nat Methods* 2005, 2(2):105-111; Zhao X D et al. "Whole-genome mapping of histone H3 Lys4 and 27 trimethylations reveals distinct genomic compartments in human embryonic stem cells" *Cell Stem Cell* 2007, 1(3):286-298).

A robust method that adopts barcoded adaptors to generate barcoded Paired-End Ditag (bPED) libraries from genomic, chromatin immunoprecipitation (ChIP)-enriched, or transcriptomic sequences has been published in US Patent Application Publication No. 2011/0015096, which is incorporated herein by reference in its entirety. The method has demonstrated how various bPED libraries, each labeled with a unique internal barcode, can be combined to form a multiplex barcoded Paired-End Ditag (mbPED) library for ultra high-throughput sequencing. The advantages of the mbPED approach include: 1) it dramatically simplifies the experimental procedure because multiple bPED libraries can be manipulated as a single mbPED library during sequencing library preparation and sequencing; 2) it is extremely cost effective, especially for sequencing, because sequencing multiple libraries separately would otherwise cost a fortune; 3) it saves time and labor; and 4) it reduces cross-library bias because all bPED libraries in the mbPED library are treated with the same procedure.

However, there remains a need in the art for improving the efficiency of bPED library constructions, especially in connection with the design and preparation of barcoded adaptors.

SUMMARY OF THE INVENTION

In one aspect, the invention relates to a method of generating a barcoded Paired-End Ditag (bPED) nucleic acid fragment, which comprises:

(a) performing a first ligation by ligating a half-adaptor having one or two 3'-overhanging ends to a target nucleic acid to obtain a nucleic acid fragment with two ends each attached to one of the half-adaptor, the half adaptor comprising a half-barcode and a restriction enzyme (RE) recognition site;

(b) performing a second ligation by ligating two of the half-adaptor at the two ends of the nucleic acid fragment to form a circularized nucleic acid construct, wherein the circularized nucleic acid construct comprises a full-size barcoded adaptor; and (c) digesting the circularized nucleic acid construct with a RE that cleaves at a defined distance from the RE recognition site, and thereby generating the bPED nucleic acid fragment, wherein the bPED nucleic acid fragment comprises:
 (i) the full-size barcoded adaptor, comprising:
  1) a barcode, comprising a virtual or a user-defined known nucleotide sequence; and
  2) 5' and 3'flanking nucleotide sequences, each of the flanking nucleotide sequences comprising the RE recognition site;
 (ii) a first tag; and
 (iii) a second tag, covalently linked to the first tag via the full-size barcoded adaptor;
 wherein the first and the second tags are the 5'- and 3'-ends of the target nucleic acid from which the two tags originate, and wherein the length of the half-adaptor is adapted to allow the length of bPED nucleic acid fragment fits one-step sequencing.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

The present invention is more particularly described in the following examples that are intended as illustrative only since numerous modifications and variations therein will be apparent to those skilled in the art. Various embodiments of the invention are now described in detail. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "barcode" shall generally mean a virtual or a user-defined known nucleotide sequence that is used as a fingerprint for labeling a DNA fragment and/or a library and for constructing a multiplex library. The library includes, but not limited to, genomic DNA library, cDNA library and ChIP library. Libraries, of which each is separately labeled with a distinct barcode, may be pooled together to form a multiplex barcoded library for performing sequencing simultaneously, in which each barcode is sequenced together with its flanking tags located in the same construct and thereby serves as a fingerprint for the DNA fragment and/or library labeled by it. A "barcode" is positioned in between two restriction enzyme (RE) recognition sequences. A barcode may be virtual, in which case the two RE recognition sites themselves become a barcode. Preferably, a barcode is made with a specific nucleotide sequence having 0 (i.e., a virtual sequence), 1, 2, 3, 4, 5, 6, or more base pairs in length. The length of a barcode may be increased along with the maximum sequencing length of a sequencer. For example, 5500xl SOLID™ sequencer can only sequence up to 75 bp of DNA constructs, thus the length of a barcode for making bPED should take into account the current limitation that bPED sequences are limited to 75 bp. If a sequencer machine can sequence longer than 75 bp someday, the barcode length may be increased accordingly.

As used herein, "a virtual sequence" shall generally mean not in actual form (e.g., 0 nucleotide).

As used herein, "fingerprint" shall generally mean a distinctive or identifying mark or characteristic.

As used herein, the terms "restriction enzyme recognition site", "restriction enzyme binding site" and "restriction site" are interchangeable.

The terms "barcoded adaptor" and "barcoded adaptor sequence" are interchangeable.

The terms "barcode" and "barcode sequence" are interchangeable.

"A barcoded adaptor" comprises a barcode franked by two type II restriction enzyme recognition sites (e.g. MmeI). A barcoded adaptor may comprise: i) a barcode, comprising a virtual or a user-defined nucleotide sequence; ii) a first nucleotide sequence, comprising a first restriction enzyme (RE) recognition site; and iii) a second nucleotide sequence, comprising a second RE recognition site and covalently linked to the first nucleotide sequence via the barcode; wherein the first and the second REs are the same or different and they each lead to cleavage of a nucleic acid sequence at a defined distance from their respective recognition sites.

A "half-adaptor" consists of one half of a full-size (full-length) barcoded adaptor. When two "half-adaptors" are attached to two different ends of a DNA fragment ligate, a circular DNA labeled with a full-size barcoded adaptor may be subsequently generated. Two oligos may be annealed to form a single-type of half-adaptor (i.e., homogeneous half-adaptors), which is then ligated to a DNA to generate a DNA with two ends labeled with homogeneous half-adaptors (i.e., the same half-adaptor ligated to the two ends of the DNA fragment). Alternatively, more than two oligos are annealed to obtain more than one type of half-adaptor, such as two different half-adaptors, which are then ligated to a DNA fragment to generate a DNA fragment with two ends labeled with heterogeneous half-adaptors.

The terms "half adaptor" and "half-adaptor" are interchangeable.

The term "homogeneous half-adaptors" mean one single type of half-adaptor.

The term "heterogeneous half-adaptors" means at least two types of half-adaptors that have different nucleotide sequences from each other.

The first tag and the second tag mean 5'- and 3'-ends of nucleotide sequences of a target nucleic acid from which the two tags originate.

An "overhang" is a stretch of unpaired nucleotides at the end of a DNA molecule. These unpaired nucleotides can be in either 3' or 5' strand, creating either 3' or 5' overhangs. When an overhanging end is palindromic, which means the nucleotide sequence of the overhang is a palindrome.

The term "a double sticky-end half-adaptor" shall generally mean a half-adaptor with two overhang sequence. A half-adaptor with two 3'-overhanging ends belongs to a double sticky-end half-adaptor. An "imbalanced double sticky-end half-adaptor" means the two 3'-overhanging ends of the double sticky-end half-adaptor are different in length (i.e., different in the number of nucleotides within the overhang).

The term "single sticky-end half-adaptor" shall generally mean a half-adaptor with only one end having an overhang sequence.

The term "3'-T tail (or 3'-t tail)" shall mean the thymidine nucleotide is located at the 3'-end of a nucleotide sequence.

The term "3'-A tail (or 3'-t tail)" shall mean the adenine nucleotide is located at the 3'-end of a nucleotide sequence.

As used herein, "one-step sequencing" means sequencing that requires only one set of primers. Sequencing of a Mate-Paired (MP) or paired-end (as defined differently by SOLID™ systems) with SOLID™ sequencers requires two primer sets. With the bPED technology of the invention, only one set of primers is required for completely sequencing a bPED library. See U.S. Patent publication No. 20110015096, which is incorporated herein by reference in its entirety.

The invention provides an improved procedure for mbPED experiments and applications to genome-wide fusion gene identifications. A fusion gene is a chimeric gene with bizarre sequence composition and function(s). It normally consists of partial sequences of two or more "wild-type" genes, which would otherwise have normal genetic sequences and functions. With evolutionarily distant genetic sequences placed in juxtaposition, many of the fusion genes have been found to possess abnormal biological functions including tumorigenesis and cancer progression. A number of fusion genes have been identified so far, especially in cancer of various animal species. Aberrant functions of fusion genes may be resulted from misplaced regulatory sequences (e.g. promoters or enhancers) or protein-coding regions. When a regulatory sequence is misplaced in juxtaposition to another genic sequence, it may dysregulate gene expression. On the other hand, when two previously independent protein-coding regions are fused, the chimeric sequence may encode a novel protein which can potentially disrupt normal biological pathways. Chromosome instability, a hallmark of cancer, is responsible for most of the formations of fusion genes. Recurrent gene fusions through chromosome rearrangement have been reported for both solid and soft-tissue tumors. Methods for genome-wide screening of fusion genes remain limited, although ample evidence has shown a tight association between fusion genes and cancer.

In one aspect, the invention relates to a method of generating a barcoded Paired-End Ditag (bPED) nucleic acid fragment, which comprises:

(a) performing a first ligation by ligating a half-adaptor having one or two 3'-overhanging ends to a target nucleic acid to obtain a nucleic acid fragment with two ends each attached to one of the half-adaptor, the half adaptor comprising a half-barcode and a restriction enzyme (RE) recognition site;

(b) performing a second ligation by ligating two of the half-adaptor at the two ends of the nucleic acid fragment to form a circularized nucleic acid construct, wherein the circularized nucleic acid construct comprises a full-size barcoded adaptor; and (c) digesting the circularized nucleic acid construct with a RE that cleaves at a defined distance from the RE recognition site, and thereby generating the bPED nucleic acid fragment, wherein the bPED nucleic acid fragment comprises:

(ii) the full-size barcoded adaptor, comprising:
  3) a barcode, comprising a virtual or a user-defined known nucleotide sequence; and
  4) 5' and 3'flanking nucleotide sequences, each of the flanking nucleotide sequences comprising the RE recognition site;
(ii) a first tag; and
(iii) a second tag, covalently linked to the first tag via the full-size barcoded adaptor;
wherein the first and the second tags are the 5'- and 3'-ends of the target nucleic acid from which the two tags originate, and wherein the length of the half-adaptor is adapted to allow the length of bPED nucleic acid fragment fits one-step sequencing.

In one embodiment of the invention, the half-adaptor comprises one 3'-overhanging end.

In another embodiment of the invention, the one 3'-overhanging end comprises a palindromic nucleotide sequence.

In another embodiment of the invention, the half-adaptor comprises two 3'-overhanging ends.

In another embodiment of the invention, the two 3'-overhanging ends are different in length.

In another embodiment of the invention, one of the 3'-overhanging ends comprises a thymidine (T) nucleotide at the 3'-end thereof.

In another embodiment of the invention, one of the 3'-overhanging ends consists of a thymidine (T) nucleotide at the 3'-end thereof.

In another embodiment of the invention, the target nucleic acid comprises two 3'-overhanging ends, each 3'-overhanging end comprising an adenine (A) nucleotide at the 3'-end thereof.

In another embodiment of the invention, the target nucleic acid comprises two 3'-overhanging ends, each 3'-overhanging end consisting of an adenine (A) nucleotide at the 3'-end thereof.

In another embodiment of the invention, the other 3'-overhanging end comprises a palindromic nucleotide sequence.

In another embodiment of the invention, the half-adaptor has no more than 18 or 14 nucleotides.

In another embodiment of the invention, the half-adaptor comprises two annealed oligonucleotides of SEQ ID NOs. 1 and 3 or SEQ ID NOs. 2 and 3.

In another embodiment of the invention, the half-adaptor comprises two strands of annealed oligonucleotides with one strand having and the other stand having not a phosphate group at 5'-end thereof.

In another embodiment of the invention, the half-adaptor comprises homogeneous half-adaptors.

In another embodiment of the invention, the half-adaptor comprises heterogeneous half-adaptors.

In another embodiment of the invention, the target nucleic acid is selected from the group consisting of genomic DNA, chromatin immunoprecipitation (ChIP)-enriched DNA, and transcription cDNA.

In another embodiment of the invention, the transcriptome cDNA library is generated from a normal cell or a cancer cell.

In another embodiment of the invention, the target nucleic acid is obtained from a nucleic acid sequence comprising two or more than two genes that are fused.

In another embodiment of the invention, the first tag and the second tag comprise sequences from two or more than two genes that are fused.

In another embodiment of the invention, the first tag and the second tag comprise sequences from two genes that are fused.

In another embodiment of the invention, the first and second ligations are performed in the presence of T4 ligase.

In another embodiment of the invention, the restriction enzyme cleaves the nucleic acid at ≥14 or ≥18 bp away from the recognition site.

Further in another embodiment of the invention, the length of the barcode is no shorter than 3, 4 or 5 bp.

Yet in another embodiment of the invention, the RE is selected from the group consisting of MmeI, BpuEI, AcuI, and BsgI.

EXAMPLES

Without intent to limit the scope of the invention, exemplary oligos, half adaptors, instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

The invention has improved experimental procedures for fusion gene identification by using "homogeneous half adaptors" instead of "full-sized adaptors" disclosed in the US Patent Application Publication No. 2011/0015096, making it suitable for genome-wide identification and characterization of fusion genes. As previously disclosed, a bPED library is a sequencing library composed of barcoded paired-end ditags to be sequenced. Each barcoded paired-end ditag contains two unknown sequences, tag1 and tag2, as well as a library-specific barcoded adaptor. Each barcoded adaptor contains a barcode sequence flanked by two Type II restriction enzyme (RE) recognition sites, i.e. in the form of "RE-barcode-RE".

The benefit resulted from changing a "full-sized adaptor" to a "homogeneous half adaptor" is very significant. It was discovered that when a full-sized adaptor was used, only one single ligation is needed to generate the desired circular DNA construct because the 'full-sized' adaptor already contains a full "RE-barcode-RE" structure. However, a drawback exists in such a design. That is, each end of the target DNA may ligate to a full-sized adaptor causing two or more full-sized adaptors to be ligated at the junction and thus in the circularized construct structure. When this happens, MmeI digestion can only produce one usable tag, causing the percentage of the desired ditag-containing structure to be reduced (the degree varies depending on adaptor-versus-target DNA ratio as well as other factors in the ligation reaction). The invention has resolved the aforementioned issues by discovering "sticky-end homogeneous half-adaptor (SEHHA)" strategies, including "single sticky-end homogeneous half adaptor (S-SEHHA)" (FIG. 3A) and "double sticky-end homogeneous half adaptor (D-SEHHA)" approaches (FIG. 3B).

Figure 3A:
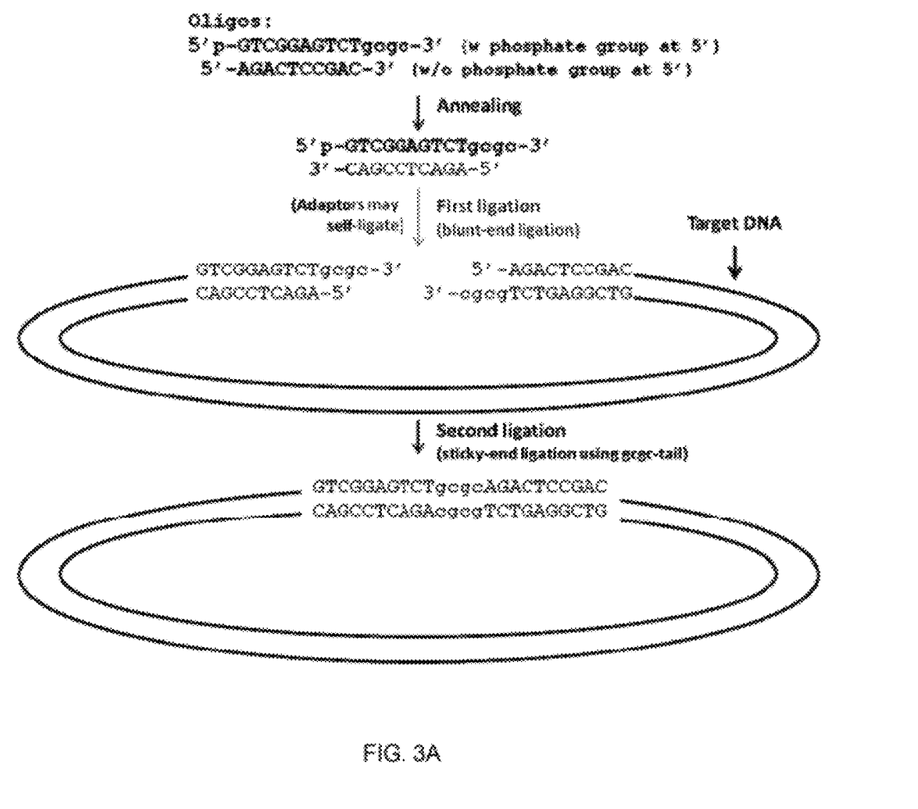
FIG. 3A is a schematic drawing showing the procedures of using a "single" sticky-end homogeneous half adaptor (S-SE-HHA) to circularize a target DNA.
Figure 3B:
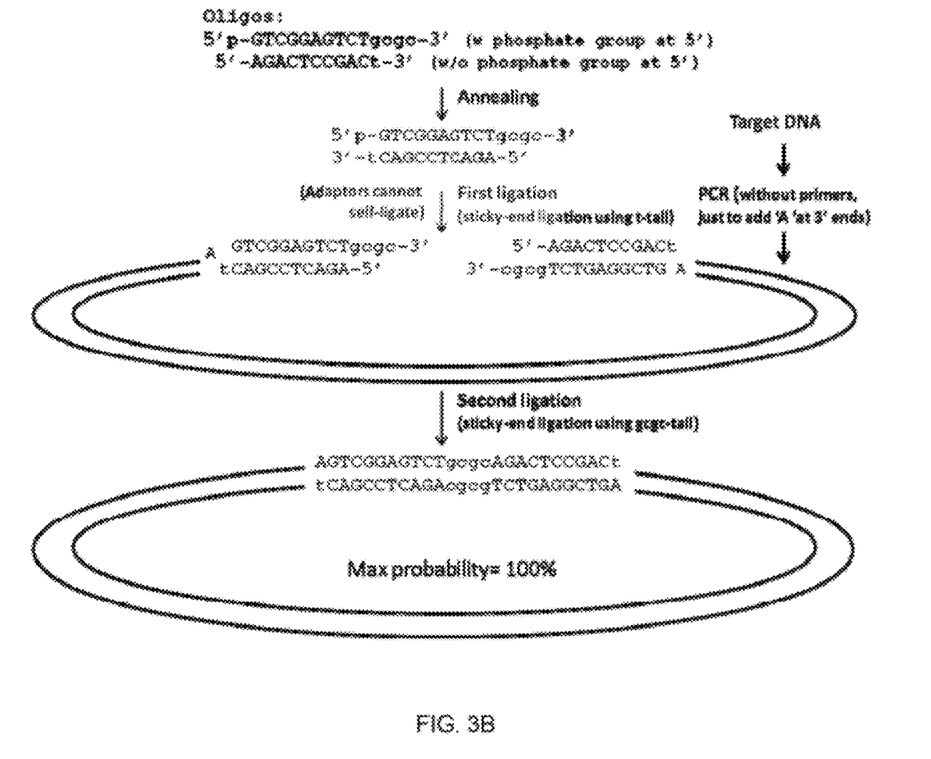
FIG. 3B is a schematic drawing showing the procedures of using a "double" sticky-end homogeneous half adaptor (D-SEHHA) to circularize a target DNA.

The SEHHA strategies offer numerous advantages: 1) The long sticky-end ('gcgc' as an example) of a half adaptor is palindromic, self-complementary, and adjustable in length; 2) Long sticky end-mediated self ligation between half adaptor molecules is completely prevented for both S-SEHHA and D-SEHHA, because only the long oligo is synthesized to have a phosphate group at the 5'end, while the short oligo has no phosphate group at the 5' end; and when they form half "adaptors", there is no phosphate group on the 'gcgc' side and thus ligation cannot occur (FIGS. 3A and 3B). The phosphate group is required for ligation to occur; 3) Adaptor self ligation through the non-gcgc side can only occur for S-SEHHA (free half-adaptor dimers may form through blunt-end ligation), but not for D-SEHHA because of the presence of 'T' (also called T-tail or t-tail) in the short oligo. This 'T' needs to pair with an 'A', which is not present in the half adaptor; 4) The half adaptor molecules are homogeneous (i.e., of the same nucleotide sequence) and have equal opportunities to bind to target DNA ends; 5) During the first ligation, binding of half adaptors to target DNA ends is directional (i.e., only the non-gcgc side can ligate to the ends of the target DNA) and in 1:1 molar ratio; and 6) During the second ligation, inclusion of more than one full-sized adaptor can be completely prevented by D-SEHHA.

Figure 1:
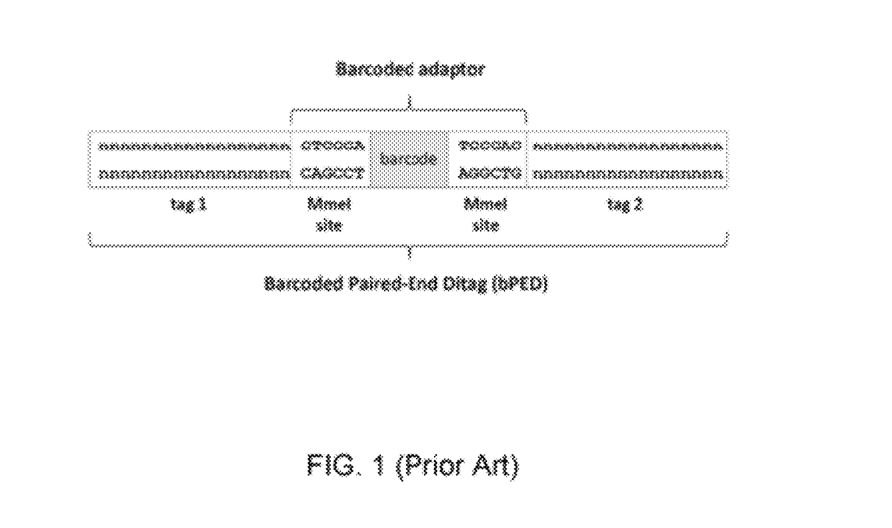
FIG. 1 is a schematic drawing showing a barcoded paired-end ditag (bPED).

FIG. 1 shows the structure of a barcoded paired-end ditag of a bPED library. The barcoded adaptor consists of a library-specific barcode flanked by two homogeneous (or heterogeneous) Type II restriction enzyme (RE) sites (such as MmeI sites). The barcoded paired-end ditags of a bPED library are the end products of a series of experimental procedure involving adaptor preparation, ligation, and digestion of circularized constructs with RE (e.g., MmeI).

Figure 2:
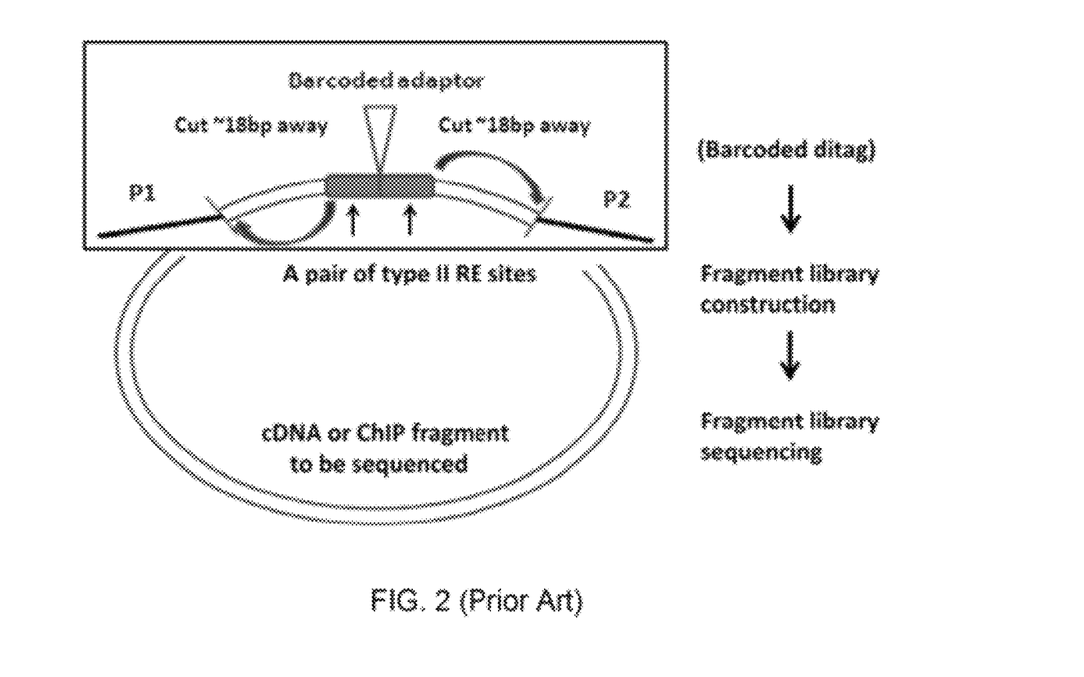
FIG. 2 is a schematic drawing showing construction of a bPED nucleic acid fragment library.

In more detail, oligos have to be designed and synthesized based on the desired barcode and Type II enzyme site in the adaptor sequence. The long oligo, but not the short oligo, should carry a phosphate group at the 5' end (see FIGS. 3A and 3B). The single-stranded oligos are annealed and mixed to form double-stranded barcoded adaptors. Subsequently, these library-specific adaptors are ligated to target DNA molecules of various sequences in the library to form circular constructs. Incubation of the desired Type II restriction enzyme with the preparation would result in the cleavage of bPED sequences from the circular constructs (FIG. 2). Thus, the barcode sequence has a direct physical association with the ditag sequences in the bPED structure and is able to function as a library-specific fingerprint to represent the whole library, because all bPED sequences are uniformly labeled with the same barcode.

FIG. 2 shows formation of barcoded paired-end ditags of a bPED library. Barcoded paired-end ditags (bPEDs) of a bPED library are generated by Type II restriction enzyme digestion of circular constructs containing a barcoded adaptor (including a library-specific barcode and two restriction sites) ligated to target DNA molecules. Restriction enzyme digestion releases two terminal tag sequences from the insert and a bPED fragment is thus generated. The bPED library, which in fact carries paired-end (or so-called 'Mate-Paired (MP)' for SOLID™ system) information, can simply be treated as a fragment library.

1. Technical Improvement for Construction of Barcoded Paired-End Ditag (bPED) Library The efficacy of bPED library production is influenced by many factors, including adaptor design, ligation, target DNA preparation, and RE digestion, etc. Among these factors, adaptor design and ligation have been found to be the most critical step. As such the inventive efforts has been focused on enhancing ligation efficiency and significant achievements have been made, especially for adaptor designs, adaptor sequence engineering and ligation of adaptor sequences to target DNAs. After a series of sequence design and experiments using SmaI-linearized pBluescript and pT/A vectors (Yestern) as experimental target. DNAs, it was found that half adaptors (which have to be coupled with two ligation steps) worked better than full-sized adaptors (which have to be coupled with a single ligation step). It was also discovered that homogeneous half-adaptors worked better than heterogeneous half-adaptors (data not shown).

Adaptor Design and Adaptor Sequence Engineering

Various types of "half adaptor" designs were tested and the following discoveries were made: 1) in general, sticky end half adaptors design worked better than blunt-end half adaptors; 2) both double sticky-end half adaptor (e.g., having an extra base 'T' at the 3' end of the short oligo) and single sticky-end half adaptor (without the extra 'T') work well; and 3) adaptor length affects bPED production efficacy (data not shown). Since adaptors were generated through hybridization of oligos, single-stranded oligos were synthesized and paired accordingly.

Ligation of Adaptor Sequences to Target DNAs

All half-adaptor designs need to be coupled with two ligation steps to generate a circular construct containing a target DNA insert. A half-side of a full adaptor (i.e., a half adaptor) is first ligated to target DNAs, either by sticky-end ligation (using double sticky-end half adaptor) or blunt-end ligation (using single sticky-end half adaptor), which is followed by a second (all sticky-end) ligation to circularize the DNA construct. Various ligases and ligation conditions have been tested. It was found that T4 ligase worked better than quick ligase and in general, overnight ligation worked efficiently.

FIGS. 3A and 3B illustrate procedures for using either single sticky-end half adaptor (FIG. 3A) or double sticky-end half adaptor (FIG. 3B) to circularize a target DNA. The short oligo, using 5'-AGACTCCGAC-3' (SEQ ID NO: 1) as an example, can be made without (FIG. 3A) or with an extra T (FIG. 3B, 5'-AGACTCCGACt-3'; SEQ ID NO: 2, "t" shown in lower case to indicate that it is a sticky end) for making a single sticky-end half adaptor (FIG. 3A) or a double sticky-end half adaptor (FIG. 3B), respectively. The long oligo, 5'p-GTCGGAGTCTgcgc-3' ('p' stands for phosphate group), SEQ ID NO: 3, comprises a sequence complementary to the short oligo in addition to having a sticky overhand, gcgc. The two oligos (SEQ ID NO: 1 or 2 and SEQ ID NO: 3) were then annealed to produce a single type of (homogeneous) half adaptors. During the first run of ligation with the target DNA molecules, the adaptor ligates to both ends of the target DNA. The second run of ligation circularizes the DNA construct. The long sticky ends used for the second ligation are indicated by the lower case, while the underlines indicate MmeI RE sites. The maximum successful rate can be 100%.

Production of MmeI Digested Fragments

Figure 4:
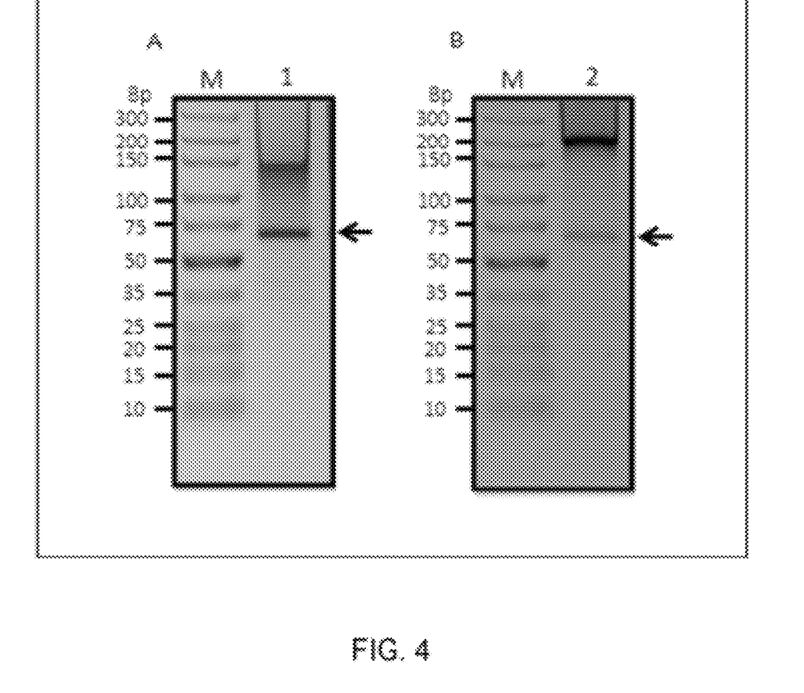
FIG. 4 is a photograph of agarose gel electrophoresis showing the expected 62 bp bands generated by MmeI digestion of constructs circularized by single sticky-end (A) and double sticky-end homogeneous half-adaptors (B), respectively.

To demonstrate the feasibility of half adaptor generated bPED technology, E. coli genomic DNA (gDNA) were sonicated to 150-500 bp and used either double sticky-end (homogeneous) half adaptor or single sticky-end half adaptor (sequences shown in FIG. 3) to circularize the E. coli gDNA. As expected, digestion of the E. coli gNDA with MmeI produced the desired ~62 bp fragment in both cases (FIG. 4). MmeI digested fragments of the same size have been generated from various DNAs, including the transcriptomic DNA and genomic DNA from human cancer cell line MCF7 and PCR fragment amplified from a vector. Some of the ~62 bp MmeI fragments have been confirmed by sequencing (data not shown).

FIG. 4 shows the results of using a single sticky-end homogeneous half adaptor (S-SEHHA) and a double sticky-end homogeneous half adaptor (D-SEHHA), respectively, to circularize sheared E. coli gDNA. Panel A) Lane M: DNA marker. Lane 1: MmeI digest of E. coli gDNA circularized with a single sticky-end half adaptor formed by oligos 5'p-GTCGGAGTCTgcgc-3' ('p' stands for phosphate group) (SEQ ID NO: 3) and 5'-AGACTCCGAC-3' (SEQ ID NO: 1). Under this circumstance, the first ligation is performed by blunt-end ligation of the half adaptor to the target DNA which does not require A-tailing by PCR, while the second ligation is mediated by complementarity between the sticky gcgc-tails. Arrow points to the expected 62 bp band. Panel B) M: DNA marker. Lane 2: MmeI digest of E. coli gDNA circularized with a double sticky-end half adaptor formed by oligos 5'p-GTCGGAGTCTgcgc-3' (SEQ ID NO: 3) and 5'-AGACTCCGACt-3' (SEQ ID NO: 2). The extra base 'T' (T-tail or t-tail, shown as 't' in the oligo sequence SEQ ID NO: 2) in the double sticky-end half adaptor forms a complementary pair with the added extra A-tail in the target DNA molecule. Under this circumstance, the first ligation is mediated by the sticky t-tail in the half adaptor and an extra 'A' in the target DNA which can be added by PCR. Similar to the second ligation of single sticky-end half adaptor, the second ligation is mediated by complementarity between the sticky gcgc-tails. Arrow points to the expected 62 bp band. Ten micrograms of E. coli gDNA was used as the starting material for each case.

II. Application of bPED Approach for Fusion Gene Screening

Figure 5:
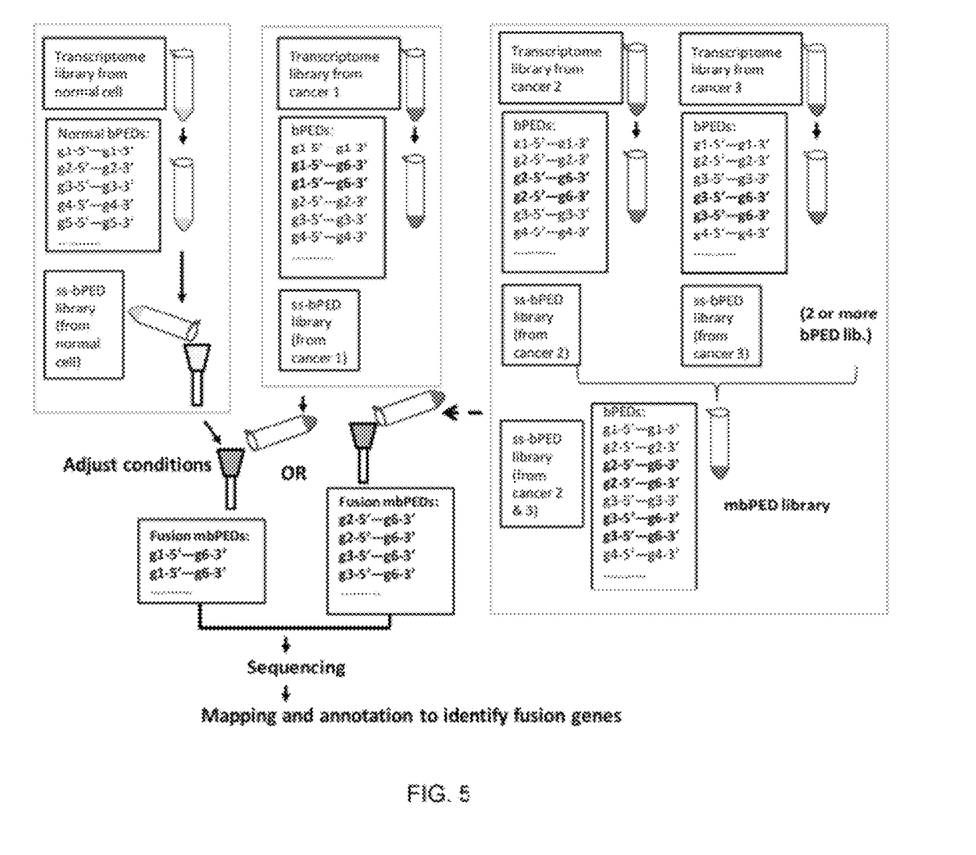
FIG. 5 is a schematic drawing showing library subtraction procedures for fusion bPEDs enrichment.

The bPED technology, originally designed for ultra high throughput sequencing, can be applied to a number of biological investigations. Besides mbPED which has been described previously, fusion gene identification is another important application. To illustrate bPED application in fusion gene identification, we utilized a bPED library generated from normal cell transcriptomes to subtract a bPED library or mbPED library, which contains multiple bPED libraries, generated from cancer transcriptomes (or other diseased cells), so to enrich "fusion bPEDs", or chimeric bPEDs, generated from fusion genes in cancer cells (FIG. 5). Subsequent sequencing (which can be performed by a traditional sequencer) followed by mapping and annotation of the chimeric fusion bPEDs against a (normal) reference genome would reveal the chromosomal locations and source (parental) genes of all fusion genes in the pool. FIG. 5 is a schematic drawing showing a library subtraction procedure for fusion bPEDs enrichment. Initially a normal cell transcriptome is used to generate a bPED library which consists of only normal bPED construct species (upper left). In parallel, individual cancer or other diseased bPED libraries are generated, each labeled with a unique barcode. These cancer bPED libraries can be processed separately (center), or pooled together to form mbPED library if it is desired (upper right). For library subtraction, bPED libraries from normal cells and cancer cells need to be denatured first to form single-stranded bPEDs (ss-bPEDs). The ss-bPEDs from normal cells are then attached to a column to serve as a bait to lure chimeric ss-bPEDs from cancer cells. This is done by adding cancer ss-bPEDs into the column to allow hybridization to occur at a high salt concentration. Under this circumstance, normal ss-bPEDs can easily form stable double-stranded bPEDs (ds-bPEDs) with their complementary (normal) ss-bPEDs. However, they may also form "partially fused" ("chimeric") ds-bPEDs with chimeric ss-bPEDs having partial (most likely to be ~50%) sequence homology, if present. Subsequent library subtraction by decreasing the salt concentration would first elute out the fraction of "fusion/chimeric ss-bPEDs" because their binding to their counterparts in the column is less stable compared to normal ss-bPEDs. Single-stranded DNA molecules in the unstable fraction can be sequenced, mapped and annotated against the normal genome to identify the fusion genes (labeled in bold in FIG. 5).

Unique Features of the Invention

The invention possesses several unique features. Firstly, it is innovative to have the terminal tags of a fusion transcript being placed in a barcoded paired-end ditag structure. Secondly, bPEDs of diseased cells are subtracted by normal bPEDs so to release and thus, enrich the bPED sequences with a partial homology to the normal bPED sequences. These enriched construct species are supposed to be the "fusion bPEDs". This has never been accomplished previously. Most importantly, when mbPED library is made by combining multiple cancerous bPED libraries, each of which contains fusion genes for that particular type of cancer, multiple cancer types can be screened and manipulated simultaneously as a single library. Based on barcode sequences, bioinformatics analyses would separate the mbPED library into individual bPED libraries, allowing further analysis for each individual bPED library and for cross-library comparisons.

Existing Technologies

Cytogenetic analysis is probably the most ancient method used for the detection of chromosomal rearrangements. Using quinacrine fluorescence and Giemsa staining, Rowley J D reported the first direct observation of chromosomal rearrangement in chronic myelogenous leukemia (CML). Later, in situ hybridization and array-based comparative genomic hybridization were employed. Although during the past several decades the above-mentioned approaches led to the discovery of most of the fusion genes, these approaches haven't been able to evolve as sophisticated fusion gene identification tools due to their lack of resolution and precision, and their shortage in throughput.

During the post-genomic era, robust next-generation sequencing (NGS) technologies have practically demonstrated a number of advantages over the traditional methods. The resolution and precision now reach to the nucleotide level, combined with ultra high throughput capability. Among the sequencing-based approaches is the Paired-End diTag (PET) method. Although having a great potential to become a sophisticated fusion gene identification tool, the PET approach has so far been used only for the discovery of a few fusion gene candidates, mainly due to the lack of further development. Instead, Maher et. al. recently reported an elegant sequencing-based approach, designated as integrative transcriptome sequencing (ITS), for genome-wide identification of gene fusions. This approach, which has led to the 're-discovery' of BCR-ABL1, TMPRSS2-ERG, and a number of known and novel gene fusions, heavily relies on the costly deep sequencing with both 454 and Solexa machine for making long and short sequences, respectively, as well as tedious data integration by bioinformatics means.

Advantages of the Invention Over Existing Technologies

As mentioned above, the traditional methods (either chromosome staining, in situ hybridization, array CGH, or other methods not mentioned above) have limitations in resolution, precision and throughput, leaving the ITS method being our major competitor. Compared to the ITS approach, the invention has several advantages as follows: 1) When a unique barcode is used for each library, the mbPED approach, according to one embodiment of the invention, enables simultaneously screening of multiple cancer transcriptomes with a single library subtraction; 2) The ITS approach is labor-intensive, while the mbPED library subtraction approach, according to one embodiment of the invention, is simple and straightforward; 3) The ITS approach is too expensive to be conducted by a regular laboratory because it heavily relies on costly deep sequencing. On the other hand, the mbPED approach, according to one embodiment of the invention, is very cost-effective and can be conducted by a regular laboratory because columns used for library subtraction can significantly reduce the sequencing load, and sequencing of the subtracted (fusion) bPED library can be done with traditional inexpensive sequencing machine; and 4) Noticeably, the mbPED approach can be employed to study the pathological progression of cancer when samples from different time points of the same cancer are taken and subtracted by a normal cell bPED library. As such, various fusion genes generated at different time points can be revealed along the time course.

Commercial Applications

The bPED technology may become a very useful tool for fusion gene screening. Once the protocol becomes sophisticated, commercial kits should be made to facilitate its utilization in pharmaceutical companies and academic laboratories. The kits may include normal bPED libraries made from normal human or mouse tissues, or from other animals. Diseased bPED libraries can also be made for charged commercial services. The commercialization of this biotechnology heavily relies on how sophisticated this approach will be.

All of the references cited herein are incorporated by reference in their entirety. The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of generating a barcoded Paired-End Ditag (bPED) nucleic acid fragment, comprising:
   (a) performing a first ligation by ligating a half-adaptor to a target nucleic acid to obtain a nucleic acid fragment with the half-adaptor attached to the two ends thereof, the half adaptor comprising a half-barcode and a restriction enzyme (RE) recognition site, wherein the half-adaptor is:
      (1) a single sticky-end half-adaptor with one 3'-overhanging end; or
      (2) a double sticky-end half-adaptor with two 3'-overhanging ends;
   (b) performing a second ligation by ligating the half-adaptors at the two ends of the nucleic acid fragment to form a circularized nucleic acid construct, wherein the circularized nucleic acid construct comprises a full-size barcoded adaptor; and
   (c) digesting the circularized nucleic acid construct with a RE that cleaves at a defined distance from the RE recognition site, and thereby generating the bPED nucleic acid fragment, wherein the bPED nucleic acid fragment comprises:
      (i) the full-size barcoded adaptor, comprising:
         1) a barcode, comprising no nucleotide or a user-defined known nucleotide sequence; and
         2) 5' and 3' flanking nucleotide sequences, each of the flanking nucleotide sequences comprising the RE recognition site;
      (ii) a first tag; and
      (iii) a second tag, covalently linked to the first tag via the full-size barcoded adaptor;
      wherein the first tag corresponds to the 5'-end of the target nucleic acid, and the second tag corresponds to the 3'-end of the target nucleic acid.

2. The method of claim 1, wherein the half-adaptor is a single sticky-end half-adaptor with one 3'-overhanging end.

3. The method of claim 2, wherein the one 3'-overhanging end comprises a palindromic nucleotide sequence.

4. The method of claim 1, wherein the half-adaptor is a double sticky-end half-adaptor with two 3'-overhanging ends.

5. The method of claim 1, wherein the first ligation is a sticky-end ligation.

6. The method of claim 5, wherein one of the 3'-overhanging ends comprises, or consists of, a thymidine (T) nucleotide at the 3'-end thereof.

7. The method of claim 6, wherein the target nucleic acid comprises two 3'-overhanging ends, each 3'-overhanging end comprising an adenine (A) nucleotide at the 3'-end thereof.

8. The method of claim 6, wherein the other 3'-overhanging end comprises a palindromic nucleotide sequence.

9. The method of claim 1, wherein the half-adaptor has no more than 18 nucleotides.

10. The method of claim 9, wherein the half-adaptor comprises two annealed oligonucleotides of SEQ ID NOs. 1 and 3 or SEQ ID NOs. 2 and 3.

11. The method of claim 1, wherein the half-adaptor comprises two strands of annealed oligonucleotides with one strand having and the other stand not having a phosphate group at the 5'-end thereof.

12. The method of claim 1, wherein the half-adaptor comprises homogeneous half-adaptors.

13. The method of claim 1, wherein the half-adaptor comprises heterogeneous half-adaptors.

14. The method of claim 1, wherein the target nucleic acid is selected from the group consisting of genomic DNA, chromatin immunoprecipitation (ChIP)-enriched DNA and transcriptome cDNA.

15. The method of claim 14, wherein the transcriptome cDNA is generated from a normal cell or a cancer cell.

16. The method of claim 1, wherein the target nucleic acid is obtained from a nucleic acid sequence comprising two or more than two genes that are fused.

17. The method of claim 16, wherein the first tag and the second tag comprise sequences from two or more than two genes that are fused.

18. The method of claim 1, wherein the first tag and the second tag comprise sequences from two or more than two genes that are fused and the half-adaptor comprises two 3'-overhanging ends.

19. The method of claim 1, wherein the restriction enzyme cleaves the nucleic acid at ≥14 or ≥18 bp away from the recognition site.

20. The method of claim 1, wherein the length of the barcode is selected from the group consisting of no shorter than 3 base pairs, no shorter than 4 base pairs, and no shorter than 5 base pairs.

* * * * *